United States Patent
Lilja et al.

(10) Patent No.: US 11,816,085 B2
(45) Date of Patent: Nov. 14, 2023

(54) PROGRAMMATIC DETERMINATIONS USING DECISION TREES GENERATED FROM RELATIONAL DATABASE ENTRIES

(71) Applicant: UnitedHealth Group Incorporated, Minnetonka, MN (US)

(72) Inventors: Frank W. Lilja, Pine City, MN (US); Aaron Christopher Wacker, Mound, MN (US); Carl J. Boudreau, Savage, MN (US); Danh Q. Lam, Wayzata, MN (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 502 days.

(21) Appl. No.: 16/729,995

(22) Filed: Dec. 30, 2019

(65) Prior Publication Data

US 2021/0200896 A1    Jul. 1, 2021

(51) Int. Cl.
*G06F 16/901* (2019.01)
*G06F 16/22* (2019.01)
*G06F 21/62* (2013.01)
*G16H 70/00* (2018.01)
*G06N 20/00* (2019.01)

(52) U.S. Cl.
CPC ...... *G06F 16/2282* (2019.01); *G06F 16/9024* (2019.01)

(58) Field of Classification Search
CPC .......... G06F 16/2282; G06F 16/9024
See application file for complete search history.

(56) References Cited

U.S. PATENT DOCUMENTS

| | | | |
|---|---|---|---|
| 8,265,959 B2 * | 9/2012 | McKenzie | G06Q 40/08 705/2 |
| 9,471,669 B2 * | 10/2016 | Bilinski | G06F 16/248 |
| 10,289,804 B2 * | 5/2019 | Chapman | G06Q 40/02 |
| 10,977,702 B2 * | 4/2021 | Patel | G06Q 30/0603 |
| 2007/0174252 A1 * | 7/2007 | Rawlings | G06Q 10/10 |
| 2009/0048877 A1 * | 2/2009 | Binns | G06Q 10/04 705/4 |
| 2011/0257992 A1 * | 10/2011 | Scantland | G06Q 10/10 705/2 |
| 2012/0166212 A1 * | 6/2012 | Campbell | G16H 40/20 705/2 |
| 2013/0006672 A1 * | 1/2013 | Dang | G06Q 30/02 705/2 |
| 2014/0006042 A1 * | 1/2014 | Keefe | G16H 10/20 705/2 |

(Continued)

OTHER PUBLICATIONS

"PokitDok Platform Overview," (4 pages), [online], [retrieved from the Internet Apr. 12, 2018] <URL: https://pokitdok.com/videos/pokitdok-platform-overview/>.

(Continued)

*Primary Examiner* — Miranda Le
(74) *Attorney, Agent, or Firm* — Alston & Bird LLP

(57) ABSTRACT

Methods, apparatus, systems, computing devices, computing entities, and/or the like for programmatic methodologies for determining and providing prior authorization requirements in a way that facilitates inputting information/data, updating information/data, searching information/data, viewing information/data, reporting information/data, and analyzing information/data while being broadly accessible to disparate systems.

13 Claims, 16 Drawing Sheets

(56) References Cited

U.S. PATENT DOCUMENTS

| | | | |
|---|---|---|---|
| 2015/0235002 A1* | 8/2015 | Schentag | G16Z 99/00 |
| | | | 514/23 |
| 2015/0261935 A1 | 9/2015 | Crockett | |
| 2015/0324547 A1* | 11/2015 | Graham | G16H 70/40 |
| | | | 705/2 |
| 2017/0046492 A1* | 2/2017 | Renner | G16H 10/60 |
| 2018/0005126 A1 | 1/2018 | Yamagami et al. | |
| 2019/0156955 A1* | 5/2019 | Winlo | G16H 15/00 |

OTHER PUBLICATIONS

"Prior Authorization—4 Steps To Take Now," Prior Authorization Review, 2019 Best Solutions, Services and Vendors, (19 pages), [online], [retrieved from the Internet Apr. 12, 2018] <https://www.practicesuite.com/prior-authorization/>.

"TriZetto Touchless Authorization Processing (TTAP)," TriZetto Provider Solutions, (4 pages), [online], [retrieved from the Internet Apr. 12, 2018] <https://www.trizettoprovider.com/Who-We-Serve/Payer/TTAP>.

Murthy, Sreerama K., "Automatic Constructions Of Decision Trees From Data: A Multi-Disciplinary Survey," Data Mining and Knowledge Discovery, vol. 2, No. 4, (1998), pp. 345-389.

\* cited by examiner

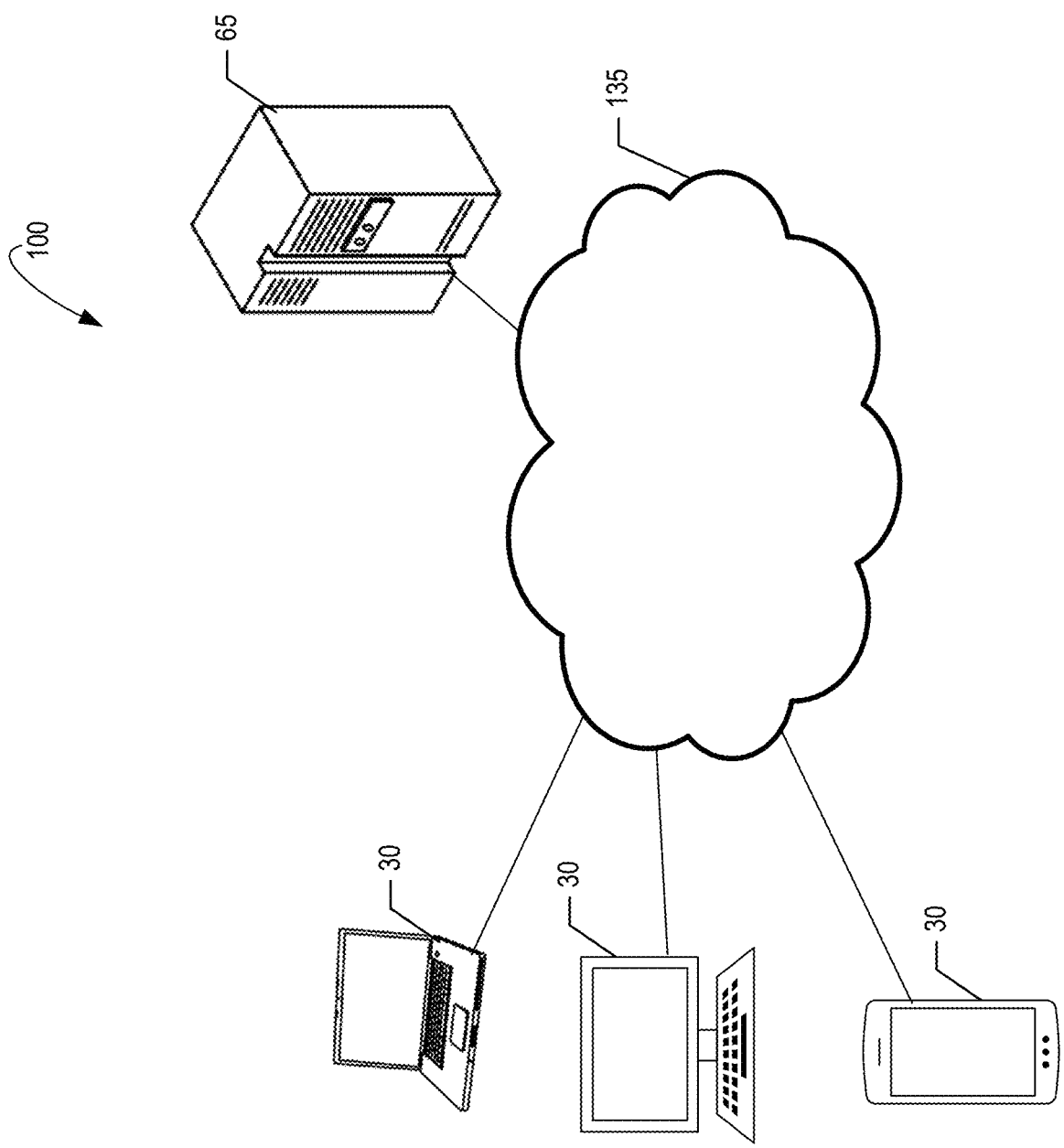

FIG. 6A

Category | Rule Decision | Procedure Code | Procedure Modifier 1 | Procedure Modifier 2 | Procedure Modifier 3 | Procedure Modifier 4 | Unclassified Drugs | State Exception

FIG. 6B

Par Non-par | Provider Type | Provider Specialty | Notification Type | Place Of Service | Revenue code | dx code from | dx code to | Patient Gender | Age Lower Limit

FIG. 6C

Patient Age Upper Limit | Count | Unit Of Measure | Frequency | total_count | day_count > day_count | eff_date | term_date

| Category | Rule Decision | Procedure Code | Procedure Modifier 1 | Procedure Modifier 2 | Procedure Modifier 3 | Procedure Modifier 4 | Unclassified Drugs | State Exception |
|---|---|---|---|---|---|---|---|---|
| Tonsillectomy and adenoidectomy | Prior Auth | 42830 | N/A | N/A | N/A | N/A | N/A | N/A |
| Tonsillectomy and adenoidectomy | No Prior Auth | 42820 | N/A | N/A | N/A | N/A | N/A | N/A |
| Tonsillectomy and adenoidectomy | Prior Auth | 42830 | N/A | N/A | N/A | N/A | N/A | N/A |

FIG. 6H

| Participation | Provider Type | Provider Specialty | Notification Type | Place Of Service | Revenue codes for each dx code | dx codes from | Patient Gender | Age Lower Limit |
|---|---|---|---|---|---|---|---|---|
| PAR | N/A | N/A | N/A | Not Ambulatory Surgery Center | Not Ambulatory Surgery Center | N/A | N/A | N/A |
| PAR | N/A | N/A | N/A | Ambulatory Surgery Center | Ambulatory Surgery Center | N/A | N/A | N/A |
| NON-PAR | N/A | N/A | N/A | N/A | ALL | N/A | N/A | N/A |

FIG. 6I

| Patient Age Upper Limit | count | Unit Of Measure | Frequency | Total count | dx count | dx code | item | item end |
|---|---|---|---|---|---|---|---|---|
| N/A | N/A | N/A | < | N/A | N/A | N/A | 10/1/2017 | 12/31/2999 |
| N/A | N/A | N/A | > | N/A | N/A | N/A | 10/1/2017 | 12/31/2999 |
| N/A | N/A | N/A | > | N/A | N/A | N/A | 10/1/2017 | 12/31/2999 |

Lines of Business

+ Add New Record    ⟳ Refresh

— 214A-N

| Line of Business | Effective Date | Term Date | | |
|---|---|---|---|---|
| C&S | 01/01/1980 | 01/01/2099 | Clients | Health Plan Products |
| CJB1 | 03/01/2018 | 03/28/2018 | Clients | Health Plan Products |
| Danh LOB temp | 02/25/2018 | 04/07/2018 | Clients | Health Plan Products |
| DQL LOB | 02/25/2018 | 03/31/2018 | Clients | Health Plan Products |
| E&I | 01/01/1980 | 01/01/2099 | Clients | Health Plan Products |
| M&R | 01/01/1980 | 01/01/2099 | Clients | Health Plan Products |
| M&V (TEST) | 01/01/2017 | 12/31/2017 | Clients | Health Plan Products |

7 Lines of Business matching your search criteria

Lines of Business per page  25 ▾

FIG. 8

C&S health plan products

— 214A-N

| HealthPlanProduct | Effective Date | Term Date | Release Status | | | |
|---|---|---|---|---|---|---|
| Alaska_Perf1 | 11/23/2016 | 03/27/2020 | In Process | Products | Rules | |
| Alaska_Perf2 | 01/01/2017 | 12/31/2099 | In Process | Products | Rules | |
| Alaska_Perf3 | 01/01/2017 | 12/31/2099 | In Process | Products | Rules | |
| Alaska_Perf4 | 10/01/2018 | 12/31/2099 | Released to Production | Products | Rules | |
| Alaska_Perf-Copy | 11/23/2016 | 03/27/2020 | In Process | Products | Rules | |
| Alaska-Copy | 01/01/2017 | 12/26/2019 | In Process | Products | Rules | |
| Alaska-Copy | 11/23/2016 | 03/27/2020 | In Process | Products | Rules | |
| Alaska-Copy1 | 01/01/2017 | 12/26/2019 | In Process | Products | Rules | |
| Alaska-Copy-Copy | 06/07/2018 | 06/13/2018 | In Process | Products | Rules | |

Health Plan Products per page 10

PROGRAMMATIC DETERMINATIONS USING DECISION TREES GENERATED FROM RELATIONAL DATABASE ENTRIES

BACKGROUND

Current methodologies for programmatically executing automatic authorizations (such as prior authorizations in the healthcare context) do not provide for the management and maintenance of prior authorization requirements in a way that is exhaustive, unambiguous, and synoptic. Further, the prior authorization requirements are not provided in a way that facilitates inputting information/data, updating information/data, searching information/data, viewing information/data, reporting information/data, and analyzing information/data while being broadly accessible to disparate systems. Because of this, current methodologies lead to inconsistencies, gaps, and errors in their implementations.

Through applied effort, ingenuity, and innovation, the inventors have developed systems and methods for the same. Some examples of these solutions are described in detail herein.

BRIEF SUMMARY

In general, embodiments of the present invention provide methods, apparatus, systems, computing devices, computing entities, and/or the like.

In accordance with one aspect, a method is provided. In one embodiment, the method comprises providing, by one or more processors, an interface enabling navigation of (a) one or more first prior authorization requirements and (b) one or more second prior authorization requirements, wherein (a) the one or more first prior authorization requirements correspond to a first medical code, and (b) the one or more second prior authorization requirements correspond to a second medical code; populating, by the one or more processors, (a) one or more fields of a first row of a relational database table with at least a portion of the one or more first prior authorization requirements and (b) one or more fields of a second row of the relational database table with at least a portion of the one or more first prior authorization requirements; populating, by the one or more processors, (a) one or more fields of a third row of the relational database table with at least a portion of the one or more second prior authorization requirements and (b) one or more fields of a fourth row of the relational database table with at least a portion of the one or more second prior authorization requirements; generating, by the one or more processors, a first decision tree for the first medical code based at least in part on the first row and the second row; generating, by the one or more processors, a second decision tree for the second medical code based at least in part on the third row and the fourth row; receiving, by the one or more processors, a prior authorization request for the first medical code; responsive to receiving the prior authorization request for the first medical code, traversing, by the one or more processors, the first decision tree to generate a prior authorization response; and providing, by the one or more processors, the prior authorization response.

In accordance with another aspect, a computer program product is provided. The computer program product may comprise at least one computer-readable storage medium having computer-readable program code portions stored therein, the computer-readable program code portions comprising executable portions configured to provide an interface enabling navigation of (a) one or more first prior authorization requirements and (b) one or more second prior authorization requirements, wherein (a) the one or more first prior authorization requirements correspond to a first medical code, and (b) the one or more second prior authorization requirements correspond to a second medical code; populate (a) one or more fields of a first row of a relational database table with at least a portion of the one or more first prior authorization requirements and (b) one or more fields of a second row of the relational database table with at least a portion of the one or more first prior authorization requirements; populate (a) one or more fields of a third row of the relational database table with at least a portion of the one or more second prior authorization requirements and (b) one or more fields of a fourth row of the relational database table with at least a portion of the one or more second prior authorization requirements; generate a first decision tree for the first medical code based at least in part on the first row and the second row; generate a second decision tree for the second medical code based at least in part on the third row and the fourth row; and receive a prior authorization request for the first medical code; responsive to receiving the prior authorization request for the first medical code, traverse the first decision tree to generate a prior authorization response; and provide the prior authorization response.

In accordance with yet another aspect, a computing system comprising at least one processor and at least one memory including computer program code is provided. In one embodiment, the at least one memory and the computer program code may be configured to, with the processor, cause the computing system to provide an interface enabling navigation of (a) one or more first prior authorization requirements and (b) one or more second prior authorization requirements, wherein (a) the one or more first prior authorization requirements correspond to a first medical code, and (b) the one or more second prior authorization requirements correspond to a second medical code; populate (a) one or more fields of a first row of a relational database table with at least a portion of the one or more first prior authorization requirements and (b) one or more fields of a second row of the relational database table with at least a portion of the one or more first prior authorization requirements; populate (a) one or more fields of a third row of the relational database table with at least a portion of the one or more second prior authorization requirements and (b) one or more fields of a fourth row of the relational database table with at least a portion of the one or more second prior authorization requirements; generate a first decision tree for the first medical code based at least in part on the first row and the second row; generate a second decision tree for the second medical code based at least in part on the third row and the fourth row; and receive a prior authorization request for the first medical code; responsive to receiving the prior authorization request for the first medical code, traverse the first decision tree to generate a prior authorization response; and provide the prior authorization response.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 1 is a diagram of an authorization platform that can be used in conjunction with various embodiments of the present invention;

FIG. 2A is a schematic of additional components of an authorization system in accordance with certain embodiments of the present invention;

Figure 5:
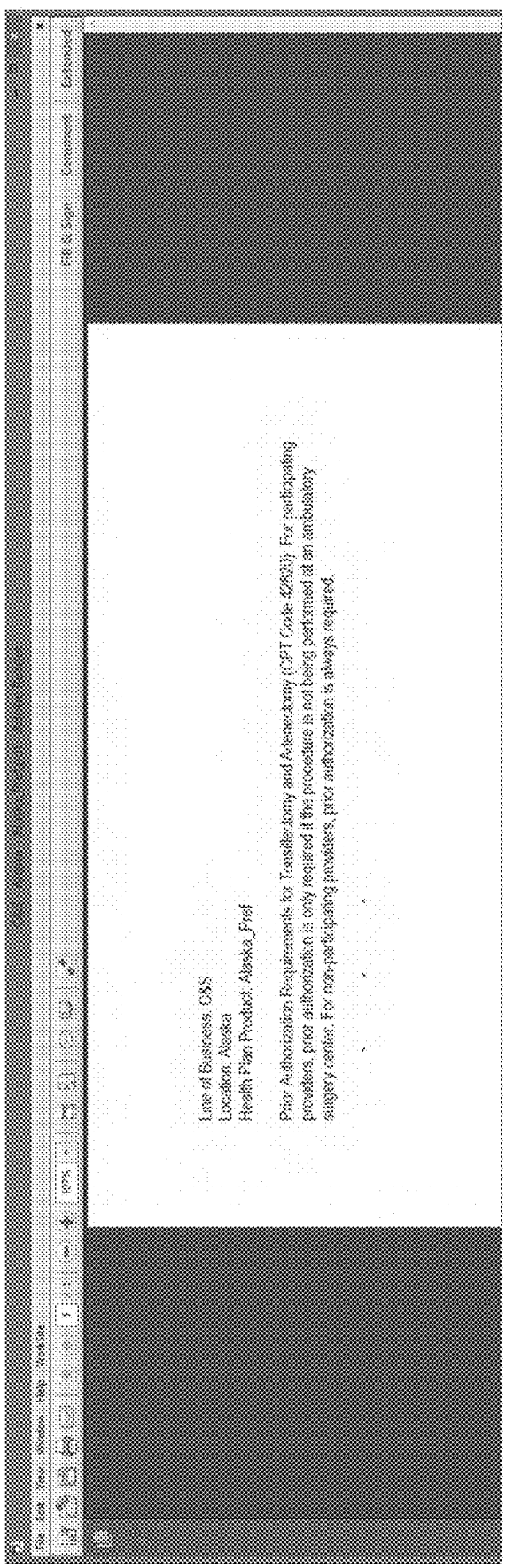
Figure 7:
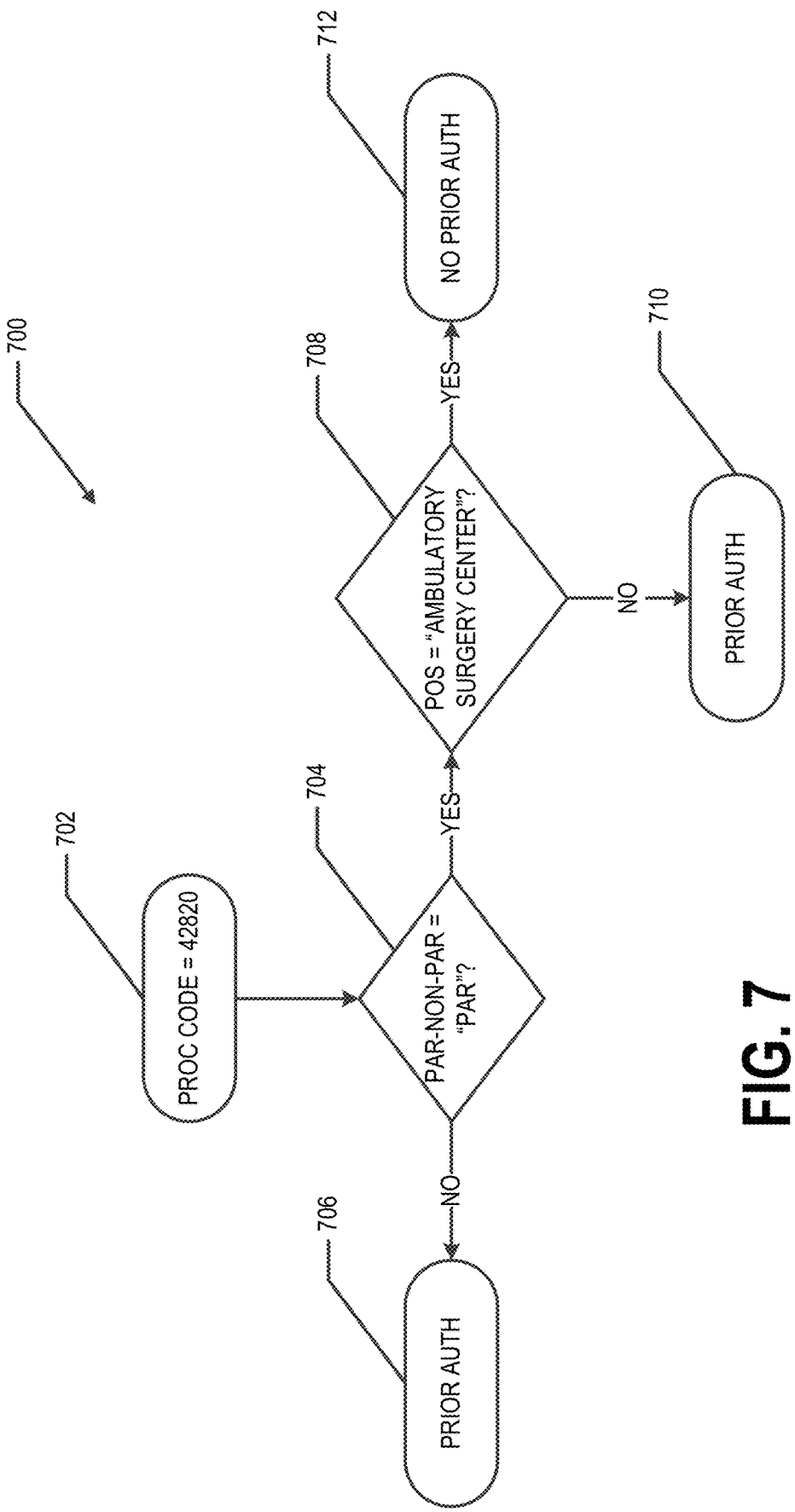

FIG. 5 comprises an exemplary contractual information/data and/or descriptive information/data for a health plan;

Figures 6D, 6E, 6F:
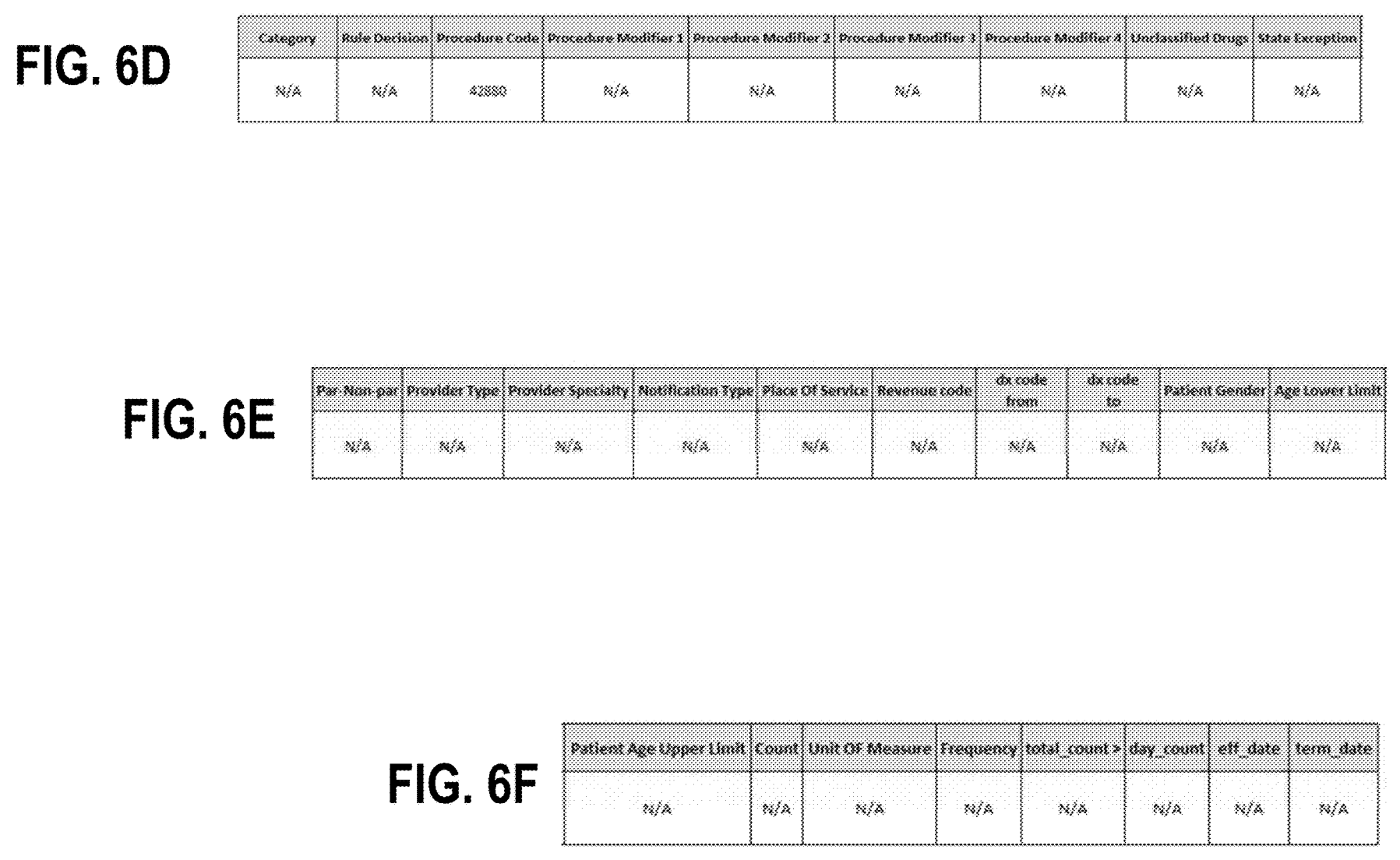

FIGS. 6A, 6B, 6C, 6D, 6E, 6F, 6G, 6H, and 6I are entries in a relational database in accordance with certain embodiments of the present invention;

FIG. 7 is a decision tree for the entries in the relational database of FIGS. 6G, 6H, and 6I, and 6C in accordance with certain embodiments of the present invention; and FIGS. 8-12 are exemplary inputs and outputs of interfaces in accordance with certain embodiments of the present invention.

DETAILED DESCRIPTION OF SOME EXAMPLE EMBODIMENTS

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" (also designated as "/") is used herein in both the alternative and conjunctive sense, unless otherwise indicated. The terms "illustrative" and "exemplary" are used to be examples with no indication of quality level. Like numbers refer to like elements throughout.

I. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. EXEMPLARY SYSTEM ARCHITECTURE

FIG. 1 provides an illustration of an authorization platform 100 that can be used in conjunction with various embodiments of the present invention. As shown in FIG. 1, the authorization platform 100 may comprise one or more authorization systems 65, one or more user computing entities 30, one or more networks 135, and/or the like. Each of the components of the system may be in electronic communication with, for example, one another over the same or different wireless or wired networks 135 including, for example, a wired or wireless Personal Area Network (PAN), Local Area Network (LAN), Metropolitan Area Network (MAN), Wide Area Network (WAN), and/or the like. Additionally, while FIG. 1 illustrate certain system entities as separate, standalone entities, the various embodiments are not limited to this particular architecture.

a. Exemplary Authorization System

Figure 2A:
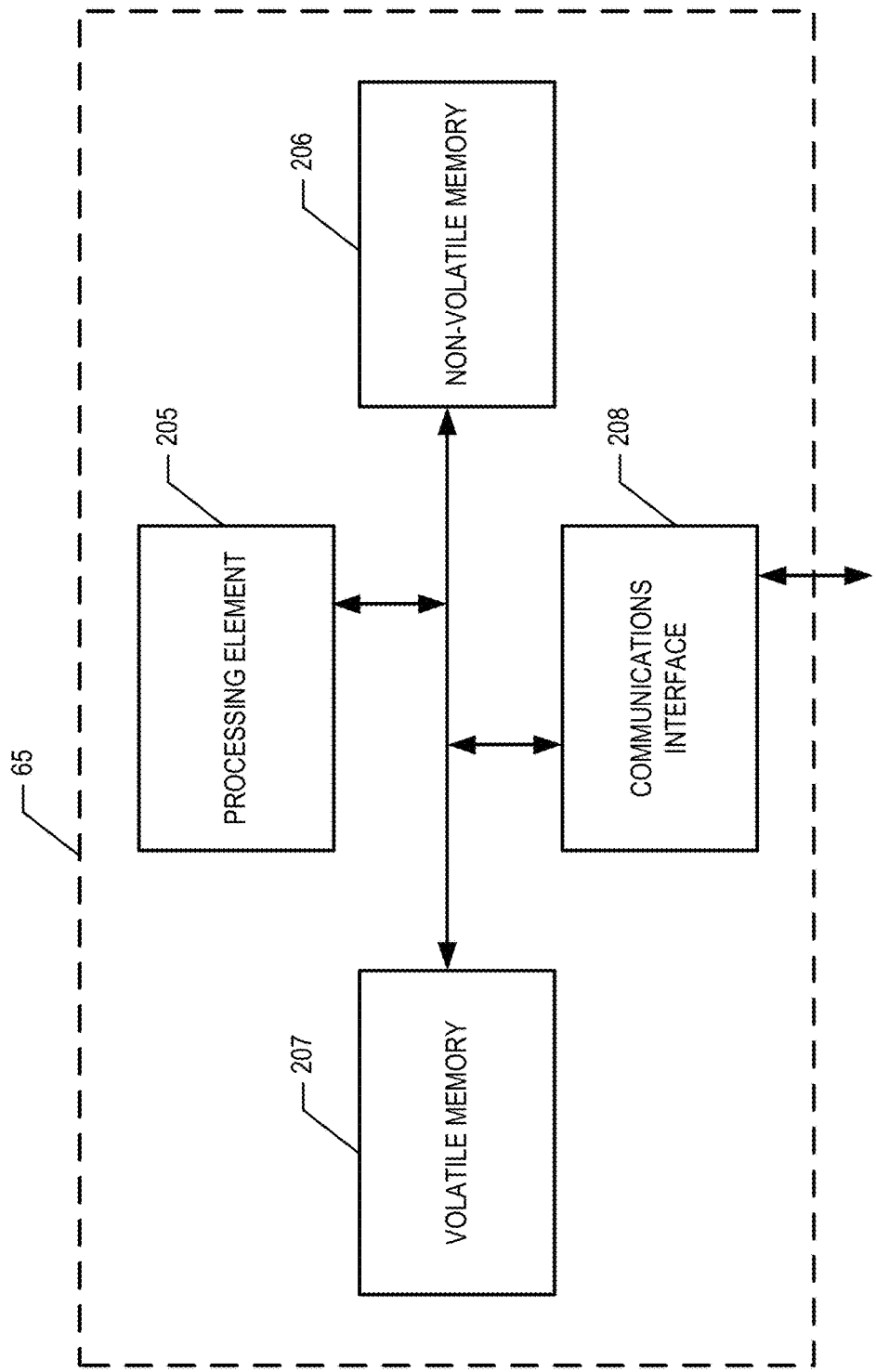
FIG. 2A is a schematic of some components of an authorization system in accordance with certain embodiments of the present invention.

FIG. 2A provides a schematic of an authorization system 65 according to one embodiment of the present invention. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the authorization system 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the authorization system 65 may communicate with other computing entities, one or more user computing entities 30, and/or the like.

As shown in FIG. 2A, in one embodiment, the authorization system 65 may include or be in communication with one or more processing elements 205 (also referred to as processors, processing circuitry, and/or similar terms used herein interchangeably) that communicate with other elements within the authorization system 65 via a bus, for example, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the authorization system 65 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 206 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, metadata repositories database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to refer to a structured or unstructured collection of information/data that is stored in a computer-readable storage medium.

Memory media 206 (may include a relational database management system (RDBMS) and one or more relational databases and/or one or more graph databases) may also be embodied as a data storage device or devices, as a separate database server or servers, or as a combination of data storage devices and separate database servers. Further, in some embodiments, memory media 206 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third party provider and where some or all of the information/data required for the operation of the authorization system may be stored. As a person of ordinary skill in the art would recognize, the information/data required for the operation of the authorization system 65 may also be partially stored in the cloud data storage system and partially stored in a locally maintained data storage system.

Memory media 206 may include information/data accessed and stored by the authorization system 65 to facilitate the operations of the system. More specifically, memory media 206 may encompass one or more relational databases and/or one or more graph databases configured to store prior authorization information/data usable in certain embodiments. In one embodiment, this relational database may be referred to as an authorization database, a prior authorization database, and/or similar words used herein interchangeably.

In one embodiment, the authorization system 65 may further include or be in communication with volatile media (also referred to as volatile storage, memory, memory storage, memory circuitry and/or similar terms used herein interchangeably). In one embodiment, the volatile storage or memory may also include one or more volatile storage or memory media 207 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 308. Thus, the databases, database instances, database management system entities, data, applications, programs, program modules, scripts, source code, object code, byte code, compiled code, interpreted code, machine code, executable instructions, and/or the like may be used to control certain aspects of the operation of the authorization system 65 with the assistance of the processing element 205 and operating system.

As indicated, in one embodiment, the authorization system 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the authorization system 65 may communicate with computing entities or communication interfaces of other computing entities, user computing entities 30, and/or the like.

Figure 2B:
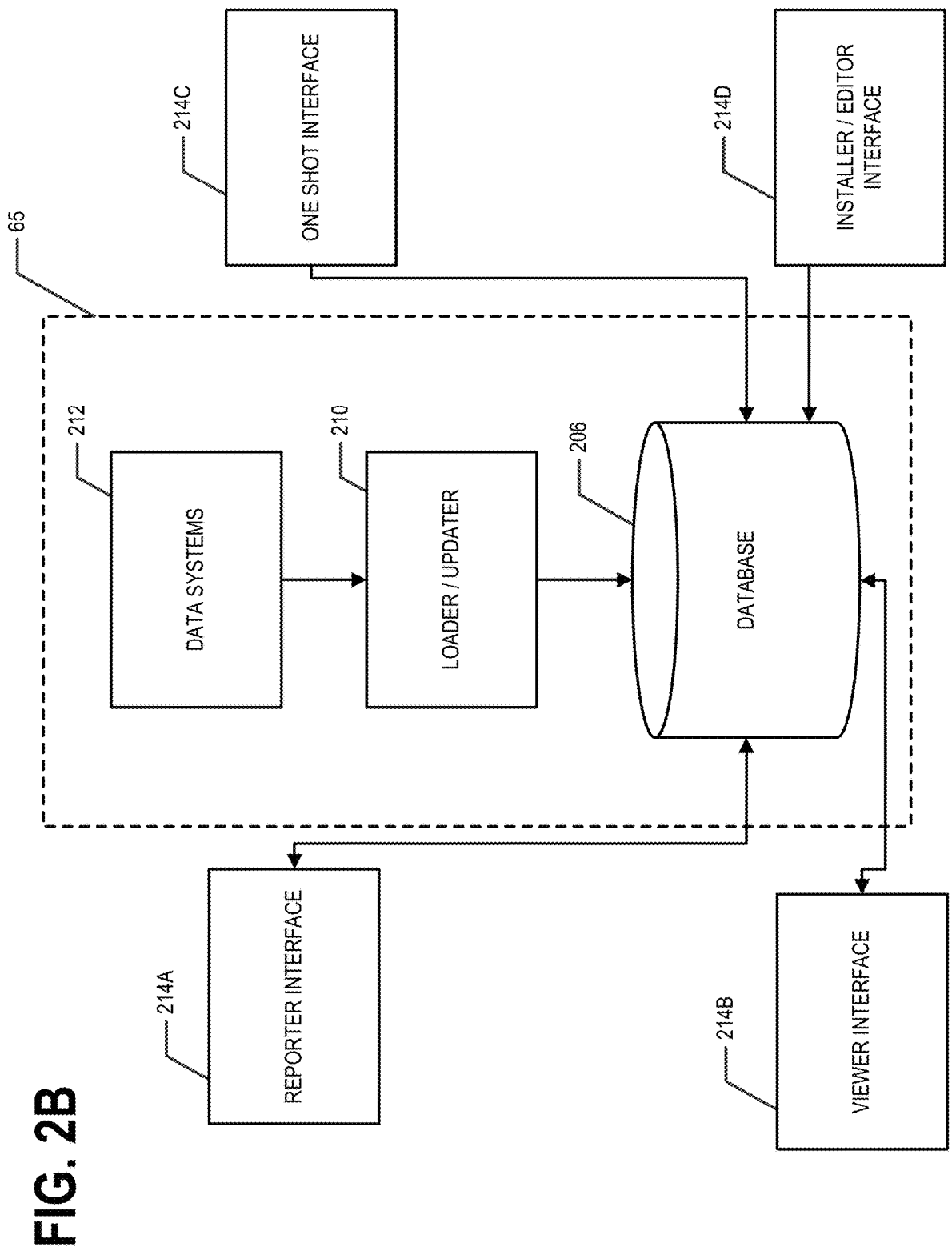

The authorization system 65 may comprise or communicate with a variety of other components, such as those shown in FIG. 2B. The components may include internal and/or external interfaces 214A-N—where in is a whole number. In one embodiment, the authorization system 65 may comprise or communicate with an installer/editor interface 214D (e.g., an authorization installer/editor). The installer/editor interface 214D may be a web interface that manages and maintains prior authorization requirements and their business products and associates business products to claims platform products. In one embodiment, the authorization system 65 may also comprise or communicate with a viewer interface 214B. The viewer interface 214B may be a web interface that presents filterable views of prior authorization requirements, business products, and associated claims platform products. The viewer interface 214B may make available prior authorization requirements for viewing, may make available prior authorization requirements listed in one or more databases as entries; and/or include a link or an application programming interface (API) connection for the same. In one embodiment, the authorization system 65 may also comprise or communicate with a reporter interface 214A. The reporter interface 214A may be a web interface for preconfigured reports and configurable reports. The reporter interface 214A may allow for data mining, comparison of business products, and/or the like.

In one embodiment, the authorization system 65 may further comprise or communicate with a one shot interface 214C. The one shot interface 214C may be a web interface that creates, updates, and deletes elements in the relational database 206 with Structured Query Language (SQL). In one embodiment, this may be because a specific functionality is not part of the installer/editor interface 214D or would otherwise be too time consuming to use. In one embodiment, the authorization system 65 may also comprise or communicate with a loader/updater 210 that (a) receives or obtains data from various data systems 212 (e.g., claims platform products) and (b) provides updates the relational database 206 with their corresponding prior authorization requirements.

As indicated, in one embodiment, the authorization system 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the authorization system 65 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The authorization system 65 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the authorization system's components may be located remotely from other authorization system 65 components, such as in a distributed system. Furthermore, one or more of the components may be aggregated and additional components performing functions described herein may be included in the authorization system 65. Thus, the authorization system 65 can be adapted to accommodate a variety of needs and circumstances.

b. Exemplary User Computing Entity

Figure 3:
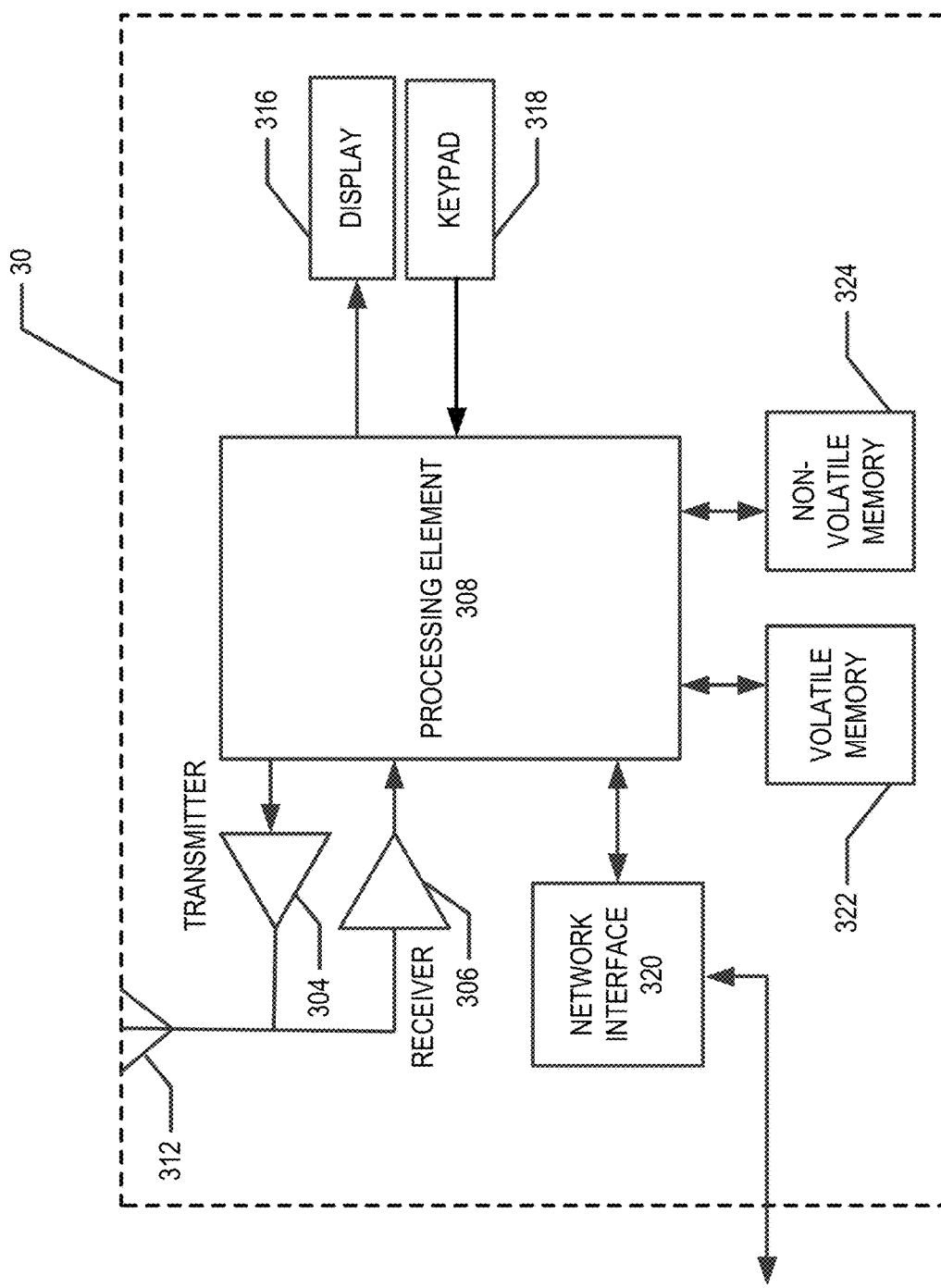
FIG. 3 is a schematic of a user computing entity in accordance with certain embodiments of the present invention.

FIG. 3 provides an illustrative schematic representative of user computing entity 30 that can be used in conjunction with embodiments of the present invention. As will be recognized, the user computing entity may be operated by an agent and include components and features similar to those described in conjunction with the authorization system 65. Further, as shown in FIG. 3, the user computing entity may include additional components and features. For example, the user computing entity 30 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as an authorization system 65, another user computing entity 30, and/or the like. In this regard, the user computing entity 30 may be capable of operating with one or more air interface standards, communication protocols, modulation types, and access types. More particularly, the user computing entity 30 may operate in accordance with any of a number of wireless communication standards and protocols. In a particular embodiment, the user computing entity 30 may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 30 can communicate with various other entities using concepts such as Unstructured Supplementary Service data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 30 can also download changes, add-ons, and updates, for instance, to its firmware, software (e.g., including executable instructions, applications, program modules), and operating system.

According to one embodiment, the user computing entity 30 may include location determining aspects, devices, modules, functionalities, and/or similar words used herein interchangeably. For example, the user computing entity 30 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data/data may be determined by triangulating the position in connection with a variety of disparate systems, including cellular towers, Wi-Fi access points, and/or the like. Similarly, the user computing entity 30 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, Near Field Communication (NFC) transmitters, and/or the like. These indoor positioning aspects can be used in a variety of settings to determine the location of someone or something to within inches or centimeters.

The user computing entity 30 may also comprise a user interface 1100 comprising one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, user interface, dashboard, webpage, and/or similar words used herein interchangeably executing on and/or accessible via the user computing entity 30 to cause display or audible presentation of information/data and for user interaction therewith via one or more user input interfaces. The user output interface may be updated dynamically from communication with the authorization system 65. The user input interface can comprise any of a number of devices allowing the user computing entity 30 to receive data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 30 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 30 can collect information/data, user interaction/input, and/or the like.

The user computing entity 30 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entity 30.

c. Exemplary Networks

In one embodiment, the networks 135 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 135 may have any suitable communication range associated therewith and may include, for example, global networks (e.g., the Internet), MANs, WANs, LANs, or PANs. In addition, the networks 135 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

III. EXEMPLARY SYSTEM OPERATION

Figure 4A:
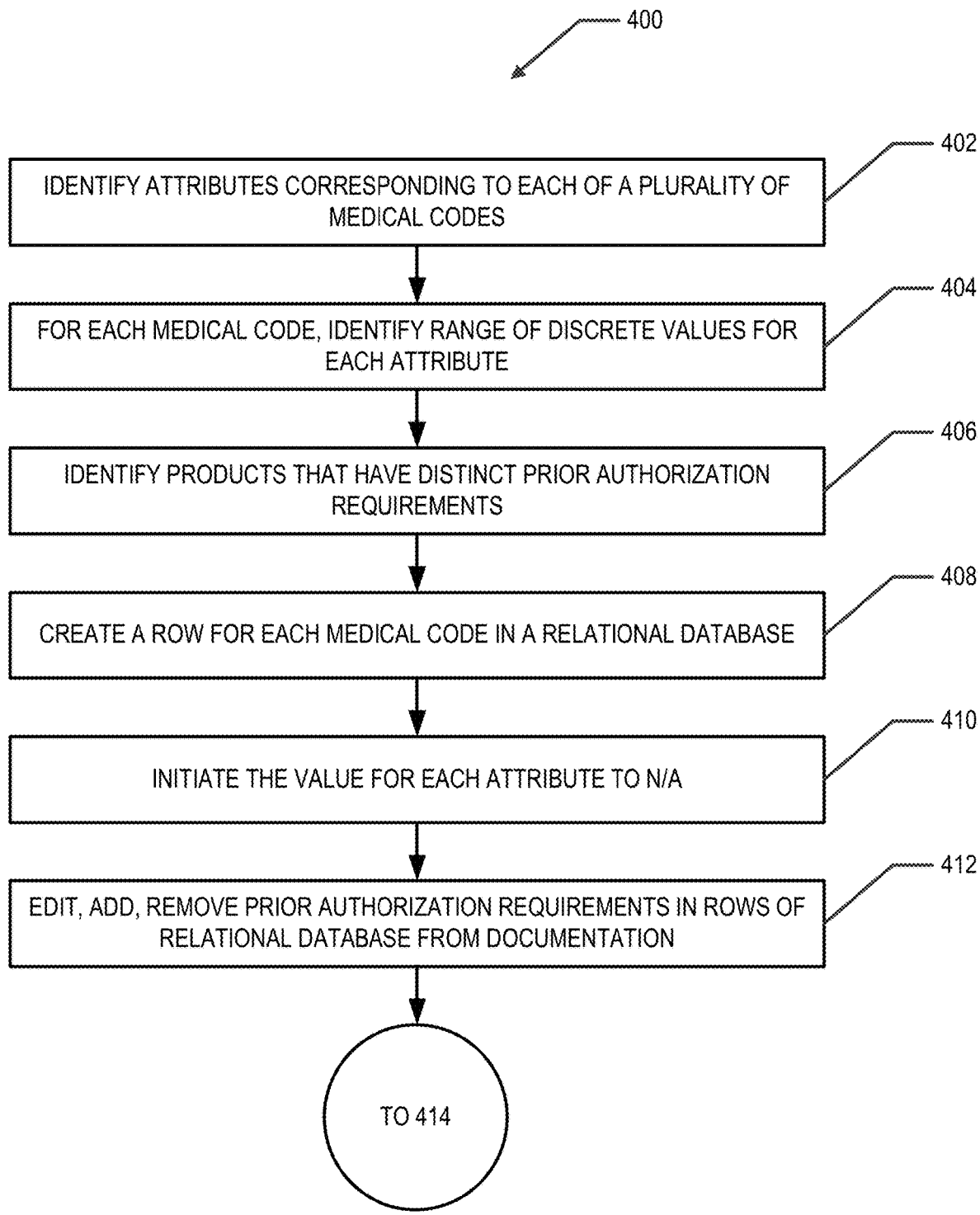
FIGS. 4A and 4B are flowcharts for exemplary connections, operations, steps, and processes in accordance with certain embodiments of the present invention.
Figure 4B:
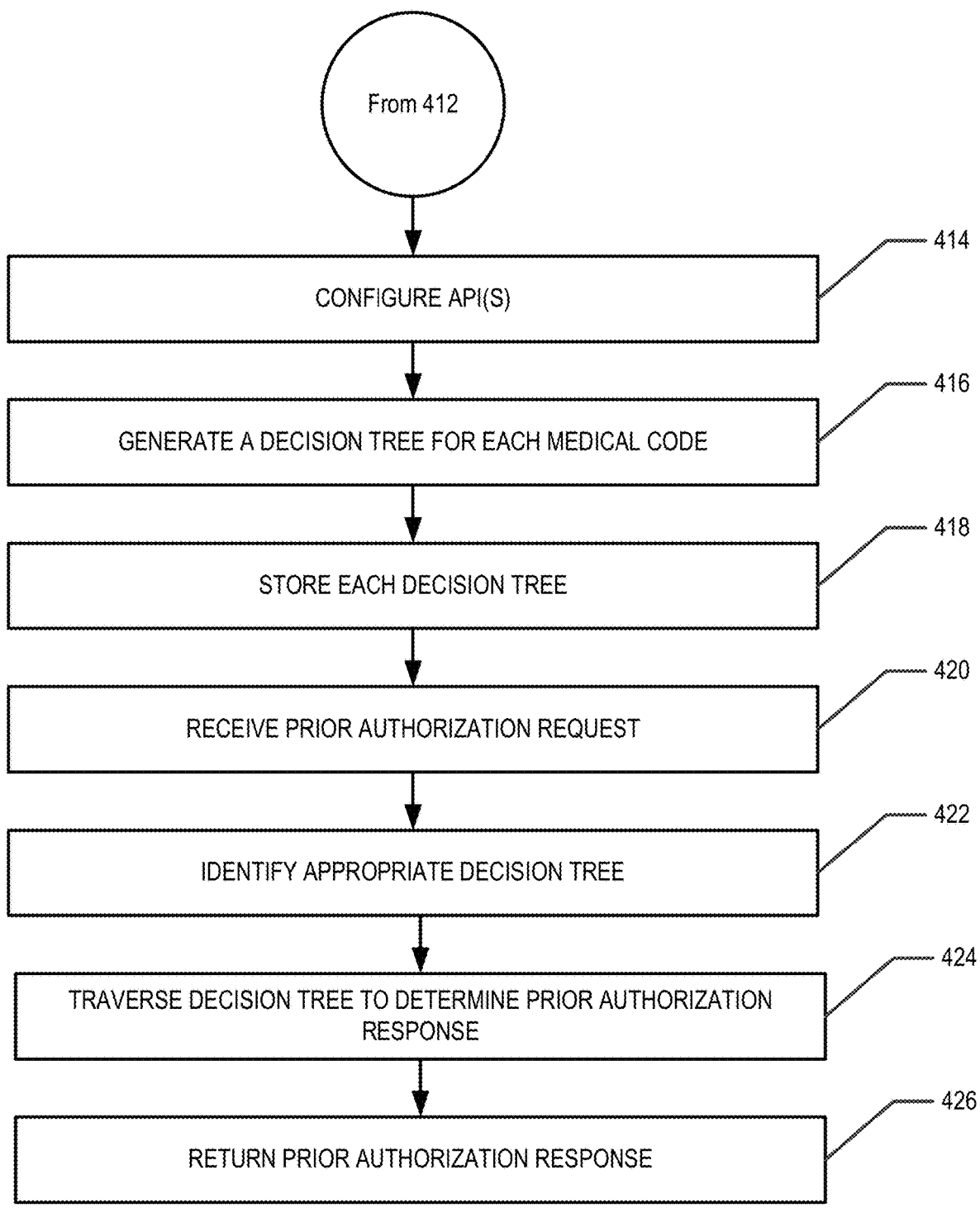

Reference will now be made to FIGS. 4A, 4B, 5, 6A, 6B, 6C, 6D, 6E, 6F, 6G, 6H, 6I, 7, and 8-12. FIGS. 4A and 4B are flowcharts for exemplary connections, operations, steps, and processes. FIG. 5 comprises an exemplary contractual information/data and/or descriptive information/data for a health plan. FIGS. 6A, 6B, 6C, 6D, 6E, 6F, 6G, 6H, and 6I are entries in a relational database. FIG. 7 is a decision tree for the entries in the relational database of FIGS. 6G, 6H, and 6I. And FIGS. 8-12 are exemplary inputs and outputs of interfaces for specific lines of business and/or products in lines of business.

a. Brief Overview

As indicated, there is a latent need for programmatic methodologies for determining and providing prior authorization (PA) requirements in a way that facilitates inputting information/data, updating information/data, searching information/data, viewing information/data, reporting information/data, and analyzing information/data while being broadly accessible to disparate systems. Embodiments described herein comprise a PA source of truth (SOT) approach that manages and maintains the PA requirements for when a PA must be requested rather than whether a PA request should be approved or denied. In one embodiment, rows/tuples in relational databases can comprise indications as to PA requirements. For example, each row may comprise an identifier for the corresponding procedures, services, products, devices, and/or the like—such as a medical/procedure code (e.g., Current Procedural Terminology (CPT) code, Healthcare Common Procedure Coding System code (HCPCS), and/or the like). All of the entries corresponding to the same medical/procedure code can be used to generate a decision tree using machine learning. The decision tree for the corresponding medical/procedure code can be stored in various forms, include as a graph data structure stored in a graph database, to facilitate traversals for determining whether a PA is required.

a.1. Technical Problems

There have been a variety of attempts to solve the problem of programmatically determining and providing PA requirements, but current methodologies are insufficient. For example, in one current approach, workflows are stored and managed to provide cross-functional processes and supporting systems. However, this approach results in process waste and increases the risk for errors. In another approach, spreadsheets and SharePoint sites are used to provide free-form text about PAs for procedures, services, products, devices, and/or the like. However, these tools are insufficient for providing consistent programmatic configurations. Big data approaches provide for more consistent responses via automated searches, but perpetuate the problem of having multiple resources or sources of PA requirements. And rules engines may be generally efficient for providing yes/no answers as to whether PAs are required; however, they are typically configured manually.

a.2. Technical Solutions

To overcome at least the above-noted technical problems, embodiments of the present invention provide an RDBMS that captures the PA requirements as attributes with their corresponding discrete values in a way that allows for efficient querying for unambiguous answers as to whether PAs are required. Further, decision trees can be generated from the entries in the RDBMS and stored as traversable graph data structures in a graph database for executing PA determinations. Additionally, the graph data structures may have one or more entry points (e.g., nodes) and/or relationships.

This approach allows for PA requirements to be programmatically distilled to a limited set of attributes with discrete values (e.g., information/data), as opposed to free form text. In this manner, salient attributes with discrete values need only be translated once so the text doesn't have to be continuously translated. This allows for ad hoc queries. Further, because the PA requirements captured in the RDBMS are not rules, the entries in the RDBMS represent the actual requirements for each PA. This approach also provides for a single SOT for all PA requirements, which enables the management and maintenance of PA requirements in a way that is exhaustive, unambiguous, and synoptic. Moreover, this approach provides a mechanism that facilitates inputting information/data, updating information/data, searching information/data, viewing information/data, reporting information/data, and analyzing information/data while being broadly accessible to disparate systems.

b. Lines of Business and/or Health Plan Products

In one embodiment, a line of business, business line, and/or similar words used herein interchangeably may refer to a product or a set of related products that serve a particular transaction or business need. In the context of embodiments of the present invention, a line of business may also have regulatory and accounting definitions to satisfy applicable laws. Further, a line of business may be associated with one or more health plan products. A health plan product may provide, offer, and/or arrange for health-related procedures, services, products, devices, and/or the like for plan members. Thus, a line of business and/or a health plan product may have contractual relationships with entities, providers, and/or the like for providing, offering, and/or arranging for health-related procedures, services, products, devices, and/or the like. In one embodiment, the authorization platform 100 can interact and communicate with various data systems 212 (e.g., claims platform products) to receive, process, manage, and maintain various PA requirements. This approach also allows external systems and internal systems to query the authorization platform 100 for a variety of purposes, such as reportings, analytics, appeals and grievances, and/or the like. This is an improvement over current systems that cannot be directly queried or even satisfactorily synchronized.

In that regard, lines of business and/or health plan products may have contractual language and/or descriptive language with regard to providing, offering, and/or arranging for health-related procedures, services, products, devices, and/or the like. Such language may also define what types of health-related procedures, services, products, devices, and/or the like require PAs before being performed or provided. FIG. 5 shows an example of a portion of contractual language and/or descriptive language for the C&S line of business in Alaska. The particular health plan product is referenced as Alaska_Pref. As can be seen, this portion of contractual language and/or descriptive language describes when PAs are required for CPT code 42820: tonsillectomies and/or adenectomies. The PA requirements for CPT code 42820 indicate that (a) PAs are only required for participating providers if the procedure is not being performed at an ambulatory surgery center, and (b) PAs are always required for non-participating providers. As will be recognized, this is an example to aid in understand embodiments of the present invention and embodiments will are described in greater detail below.

c. Identifying Attributes for Prior Authorization Requirements

In one embodiment, process 400 may begin at step/operation 402 of FIG. 4A. At step/operation 402 of FIG. 4A, attributes for corresponding to various procedures, services, products, devices, and/or the like can be identified/extracted. In one embodiment, the attributes are used to determine whether PAs are required for specific procedures, services, products, devices, and/or the like. This identification/extraction of such attributes can occur in a manual, semi-automated, and/or automated manner. Further, this identification/extraction can occur at a global level, a line of business level, and/or a health plan product level.

In a manual approach, line of business and/or health plan products can be manually reviewed via interface 214A-N to access contractual information/data, descriptive information/data, and/or the like for a line of business. For example, FIG. 8 shows an interface 214A-N providing a user (e.g., operating a user computing 30) with the ability to select or identify one or more lines of business. For instance, as an example, the C&S a line of business (e.g., a line of health plan products) is listed first under the appropriate column. The C&S line of business may be associated with an effective date, a termination date, one or more clients, one or more health plan products, and/or the like.

Continuing with the above example, FIG. 9 shows an interface 214A-N after having received user input selecting the C&S line of business. As can be seen in FIG. 9, with the C&S line of business, there are multiple associated health plan products. In FIG. 9, the health plan product names are in the first column, with the first listed health plan product being Alaska_Pref. Similar to lines of business, health plan products may be associated with effective dates, termination dates, release statuses, particular products, rules, and/or the like.

Figure 10:
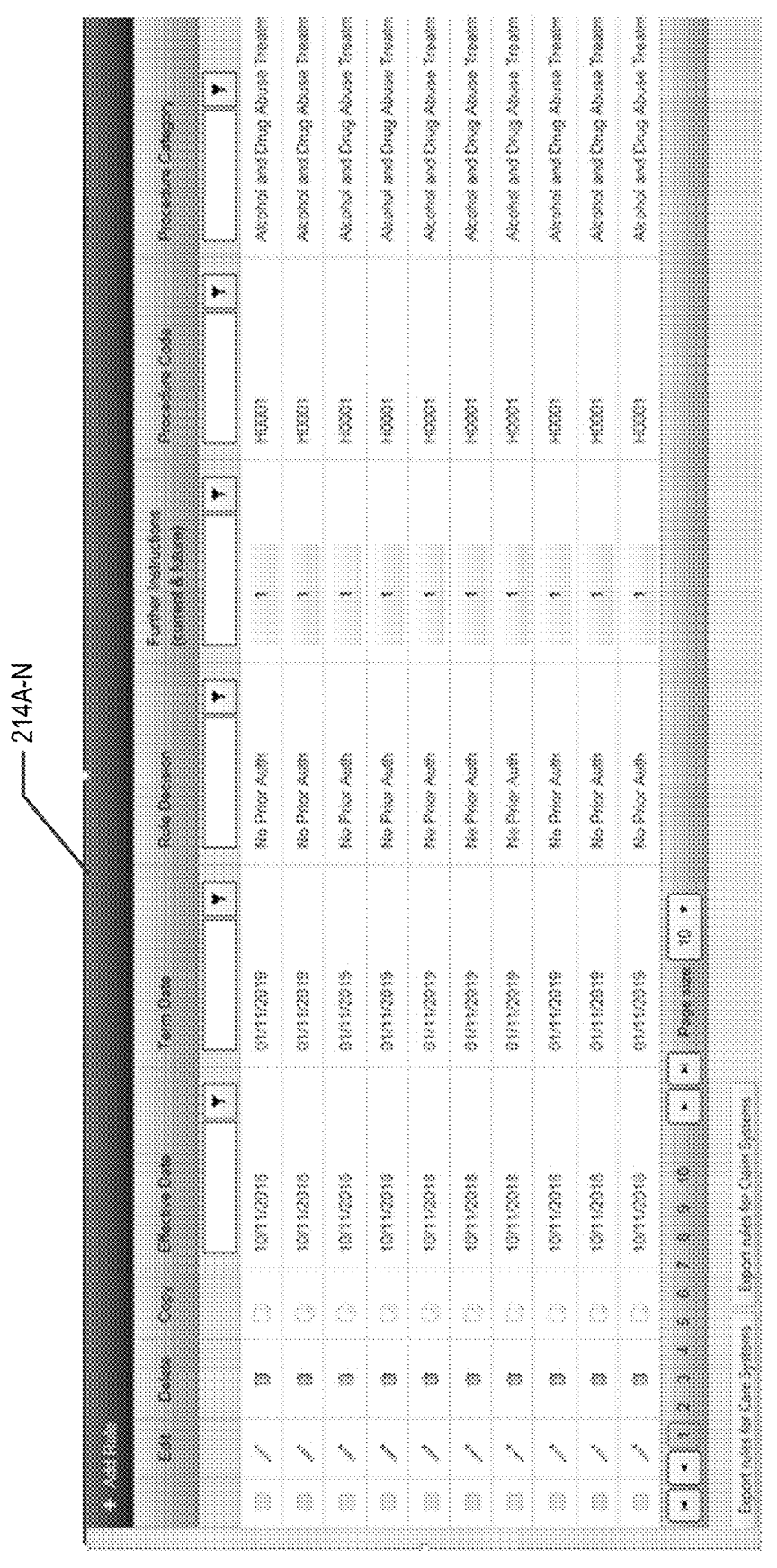

FIG. 10 shows an interface 214A-N after having received user input selecting the Alaska_Pref health plan product, for example. As can be seen in FIG. 10, with the Alaska_Pref health plan product, there are specific rules corresponding to various medical/procedure codes. The rules are interpretations of contractual information/data and/or descriptive information/data (such as that shown in FIG. 5). In the context of embodiments of the present invention, PA requirements for specific lines of business and/or health plan products can be implemented via one or more rules as defined by PA requirements. For example, as seen in FIG. 10, there are 10 rules shown as being associated with medical/procedure code H0001. In this example, each rule can be edited, deleted, and/or copied. Further, each rule may associated with an effective date, a termination date, a rule decision, further instructions, a corresponding procedure code, a corresponding procedure category, an execution order, and/or the like. These rules are an effort to enforce or comply with the contractual information/data and/or descriptive information/data for this line of business and/or health plan product.

In one embodiment, a user (e.g., operating a user computing entity 30) can review the contractual information/data, descriptive information/data, claim information/data, rule information/data, and/or the like to identify the attributes associated with each PA. Correspondingly, the user (e.g., operating a user computing entity 30) provide some form of indicia regarding the attributes. FIGS. 6A, 6B, and 6C show exemplary attributes at a global level, a line of business level, a health plan product level, medical/procedure code level, and/or the like. These exemplary attributes include a category, a rule decision (e.g., PA or no PA), one or more medical/procedure codes (e.g., CPT codes, HCPCS codes, and/or the like), one or more procedure modifiers, a participating provider indication, a non-participating provider indication, a provider type, a provider specialty, a notification type, a place of service, a revenue code, a diagnosis code to, a diagnosis code from, a patient gender, an age lower limit, an age upper limit, a count, a frequency, a total count, a day count, an effective date, a termination date, and/or the like. These attributes define the columns in the one or more RDBMSs, relational databases, relational database tables, and/or the like. With such attributes identified, in the manual approach, the user (e.g., operating a user computing entity 3) can input the attributes in one or more RDBMSs, relational databases, relational database tables, and/or the like. This process can be performed on a global level, a line of business level, a health plan product level, medical/procedure code level, and/or the like. In one embodiment, different effective dates for particular medical/procedure codes can be stored in the database to provide for a timeline of effective dates and termination dates. This will also provide for the ability to determine a given PA determination at a given point in time. Further, in some embodiments, the attributes can be defined using numerical domains for more efficient determinations, e.g., by comparing ranges or fixed numerical values for making PA determinations.

In the semi-automated approach, the authorization system 65 may use one or more natural language processing (NLP) techniques, rules engines, and/or the like to analyze contractual information/data, descriptive information/data, claim information/data, and/or rules to identify, extract, and similar words used herein interchangeably relevant attributes. The authorization system 65 may then present to the user (e.g., operating a user computing entity 30) via interface 214A-N the identified/extracted attributes for a line of business, a health plan product, medical/procedure code, and/or the like. The user (e.g., operating a user computing entity 30) can then approve, modify, and/or reject any of the identified/extracted attributes. The authorization system 65 can the input any approved attributes in one or more RDBMSs, relational databases, relational database tables, and/or the like. As with the manual approach, the semi-automated approach can be performed on a global level, a line of business level, a health plan product level, medical/procedure code level, and/or the like.

In the automated approach, the authorization system 65 may use one or more NLP techniques, rules engines, and/or the like to analyze contractual information/data, descriptive information/data, claim information/data, and/or rules to identify/extract relevant attributes. The authorization system 65 may then automatically input the attributes in one or more RDBMSs, relational databases, relational database tables, and/or the like. As with the manual and semi-automated approaches, the automated approach can be performed on a global level, a line of business level, a health plan product level, medical/procedure code level, and/or the like.

d. Identifying Discrete Values for Attributes

In one embodiment, at step/operation 404 of FIG. 4A, discrete values corresponding to the identified attributes can be identified/extracted. This identification/extraction can occur in a manual, semi-automated, and/or automated manner. Further, this identification/extraction can occur at a global level, a line of business level, and/or a health plan product level.

In a manual approach, similar to the identifying attributes, lines of business and/or health plan products can be manually reviewed via interface 214A-N to access contractual information/data, descriptive information/data, claim information/data, rule information/data, and/or the like. In one embodiment, a user (e.g., operating a user computing entity 30) can review the contractual information/data, descriptive information/data, claim information/data, rule information/data, and/or the like to identify the discrete values (e.g., range of values) associated with each attribute. For example, for a provider specialty, the discrete values associates may comprise a listing of provider specialties. Similarly, for an effective date and/or termination data, the discrete values may be limited to a particular date range. With such discrete values identified/extracted, in the manual approach, the user (e.g., operating a user computing entity 3) can configure the respective fields to only accept the discrete values for the corresponding attributes in the one or more RDBMSs, relational databases, relational database tables, and/or the like. This process can be performed on a global level, a line of business level, a health plan product level, medical/procedure code level, and/or the like.

In the semi-automated approach, the authorization system 65 may use one or more NLP techniques, rules engines, and/or the like to analyze contractual information/data, descriptive information/data, claim information/data, and/or rules to identify/extract discrete values for the attributes. The authorization system 65 may then present to the user (e.g., operating a user computing entity 30) via interface 214A-N the identified/extracted discrete values for a line of business, a health plan product, medical/procedure code, and/or the like. The user (e.g., operating a user computing entity 30) can then approve, modify, and/or reject any of the identified/extracted discrete values for the attributes. For approved discrete values, the authorization system 65 can configure the respective fields to only accept the corresponding discrete values for the corresponding attributes in the one or more RDBMSs, relational databases, relational database tables, and/or the like. This process can be performed on a global level, a line of business level, a health plan product level, medical/procedure code level, and/or the like.

In the automated approach, the authorization system 65 may use one or more NLP techniques, rules engines, and/or the like to analyze contractual information/data, descriptive information/data, claim information/data, and/or rules to identify/extract relevant attributes. The authorization system 65 can automatically configure the respective fields to only accept the corresponding discrete values for the corresponding attributes in the one or more RDBMSs, relational databases, relational database tables, and/or the like. As with the manual and semi-automated approaches, the automated approach can be performed on a global level, a line of business level, a health plan product level, medical/procedure code level, and/or the like.

e. Identifying Products and Populating Relational Database

In one embodiment, at step/operation 406 of FIG. 4A, products (e.g., lines of business and/or health plan products) with distinct PA requirements are identified. This identification can occur in a manual, semi-automated, and/or automated manner.

In a manual example, similar to the identifying attributes and discrete values, lines of business and/or health plan products can be manually reviewed via interface 214A-N to access contractual information/data, descriptive information/data, claim information/data, rule information/data, and/or the like. In one embodiment, a user (e.g., operating a user computing entity 30) can review the contractual information/data, descriptive information/data, claim information/data, rule information/data, and/or the like to identify the PA requirements associated with each health plan product, for example. For example, for CPT code 42820, each health plan product may have the same PA requirements. That is, the PA requirements for CPT code 42820 may apply globally to all lines of business and/or health care products. In other examples, each PA requirement may be global, line of business specific, health plan product specific, and/or the like. In this example (for CPT code 42820: tonsillectomies and/or adenectomies), the global PA requirements indicate that (a) PAs are only required for participating providers if the procedure is not being performed at an ambulatory surgery center, and (b) PAs are always required for non-participating providers.

At steps/operations 408 and 410 of FIG. 4A, one or more rows/tuples for each medical/procedure code (e.g., CPT code, HCPCS code, and/or the like) can be inserted in one or more RDBMSs, relational databases, relational database tables, and/or the like. And for the fields other than medical/procedure code field, each field can be populated with a null value—such as an indication "not applicable" or "N/A." As is explained below, N/A may mean not a candidate node to arrive at that particular PA requirement decision. FIGS. 6D, 6E, and 6F show all fields other than medical/procedure code field populated with a default indication of N/A. N/A indicates that the value is not applicable to determining whether a PA is required for the corresponding medical/procedure code. By initially populating these fields with "N/A," only fields later populated with discrete values other than "N/A" will be considered in generating nodes of a decision tree for making determinations as to whether a PA is required for procedures, services, products, devices, and/or the like. As will be recognized, these steps/operations can be performed in a manual, semi-automated, and/or automated manner.

At step/operation 412 of FIG. 4A, the PA requirements can be translated to populate any necessary fields with PA information/data to define the PA requirements in the one or more rows/tuples for each medical/procedure code (e.g., CPT code, HCPCS code, and/or the like). For example, the PA requirements shown in FIG. 5 for CPT code 42820 can be implemented using three rows/tuples. As previously noted, the PA requirements for CPT code 42820 indicate that (a) PAs are only required for participating providers if the procedure is not being performed at an ambulatory surgery center, and (b) PAs are always required for non-participating providers. These PA requirements are translated and populated in the three rows/tuples. FIGS. 6G, 6H, and 6I show the three rows/tuples populated with these requirements. Similar to the other figures, FIG. 6H is a continuation of FIG. 6G, and FIG. 6I is a continuation of FIG. 6H. As in this example, representing the PA requirements for a given medical/procedure code (e.g., CPT code, HCPCS code, and/or the like) may require one or more rows/tuples. However, in other examples, PA requirements may be represented using a single row. Further, as previously noted, PA requirements for each medical/procedure code (e.g., CPT code, HCPCS code, and/or the like) may occur at a global level, a line of business level, and/or a health plan product level.

In various embodiments, populating the respective fields for each medical/procedure code (e.g., CPT code, HCPCS code, and/or the like) may occur in a manual, semi-automated, and/or automated manner. Moreover, editing, adding, removing, and/or updating rows/tuples or fields can occur in a manual, semi-automated, and/or automated manner. In one embodiment, these steps/operations are performed for each medical/procedure code such that the one or more RDBMSs, relational databases, relational database tables, and/or the like become an SOT, having exhaustive and unambiguous information/data for each PA.

f. Configuration of API(s)

In one embodiment, at step/operation 414 of FIG. 4B, one or more APIs can be configured for providing requests to and receiving responses from the authorization system 65. The API requests may allow queries to the authorization system 65 to find out whether a PA is required for a particular procedure, service, product, device, and/or the like; for a particular member; with a particular provider; on a particular date; and/or at a particular location. In one embodiment, the API may be configured in a manual, semi-automated, and/or automated manner.

In one embodiment, the API requests received by the authorization system 65 and the responses provided by the authorization system 65 may be customized to adapt to various needs and circumstances. For example, in one embodiment, each API request may have all relevant attributes for a medical/procedure code (e.g., CPT code, HCPCS code, and/or the like) populated with the necessary discrete values (e.g., such as all of the attributes shown in FIGS. 6A, 6B, and/or 6C). In this example, the authorization system 65 can immediately extract the information/data from the request to make a PA determination and provide a response indicating whether a PA is required or not. In another embodiment, there may be an initial request received by the authorization system 65. In one embodiment, the initial request may identify the medical/procedure code (e.g., CPT code, HCPCS code, and/or the like), business line, and/or health plan. In the initial response, the authorization system 65 may provide the attributes that need to be populated with discrete values in a subsequent request to allow for a PA determination (e.g., such as some of the attributes shown in FIGS. 6A, 6B, and/or 6C). In this example, a subsequent request may include the relevant discrete values. The authorization system 65 can then immediately extract the information/data from the subsequent request to make a PA determination and provide a subsequent response indicating whether a PA is required or not. As indicated, a variety of other approaches and techniques can be used to adapt to various needs and circumstances.

g. Generation of Decision Trees

In one embodiment, at step/operation 416 and 418 of FIG. 4B, the authorization system 65 can apply one or more machine learning techniques and/or approaches to automatically generate one or more decision trees for each medical/procedure code (e.g., CPT code, HCPCS code, and/or the like). Each decision tree comprises one or more nodes—including a root node and one or more leaf/terminal nodes. As will be recognized, generating a decision tree for each medical/procedure code (e.g., CPT code, HCPCS code, and/or the like) may include using statements, structures, methods, mining operators, mining models, and/or the like to generate the decision trees and the corresponding nodes. This allows for more efficient decision tree generation and PA determinations and does not require a training dataset or validation dataset as would be used with other machine learning techniques and/or approaches. Further, for each attribute populated with "N/A," the authorization system 65 does not generate a node for the corresponding attribute, which results in more efficient decision tree generation and decision tree traversals.

In one embodiment, to generate a decision tree, the authorization system 65 may first identify all rows/tuples that correspond to a specific medical/procedure code (e.g., CPT code, HCPCS code, and/or the like). With all of the rows/tuples identified for a specific medical/procedure code (e.g., CPT code, HCPCS code, and/or the like), the authorization system 65 can apply one or more machine learning techniques and/or approaches based on the attributes and discrete values for the rows/tuples to generate the various nodes, the structure the tree, the indications for the determinations at some nodes, the paths to and from nodes, and the determinations at any leaf/terminal nodes.

Continuing with the above example, FIG. 7 shows an exemplary decision tree 700 automatically generated using machine learning techniques and/or approaches from the rows/tuples shown in FIGS. 6G, 6H, and 6I. In this example, to generate decision tree 700, there are six relevant attributes: (1) rule decision; (2) procedure code; (3) notification type; (4) place of service; (5) effective date; and (6) termination date. The machine learning techniques and/or approaches then determine the shortest paths to the various PA determinations, which is enable by leverage the relational database structure and representation therein of the PA requirements. For example, using the discrete values for the relevant attributes, the machine learning techniques and/or approaches define the root node as CPT code 42820. Thus, in this example, decision tree 700 may be a decision tree that applies at a global level. In other words, all requests for PA determinations for CPT code 42820 may be determined by decision tree 700. Further, in this example, as there are three rows/tuples that represent three separate determinations, there are three separate leaf/terminal nodes 706, 710, and 712 indicating PA determinations. Each of leaf/terminal nodes 706, 710, and 712 indicates whether a PA is or is not required based on the discrete values provided in the PA request.

As previously indicated, because PA requirements may apply at a global level, a line of business level, and/or a health plan product level, the respective decision trees would correspondingly apply at a global level, a line of business level, and/or a health plan product level. For instance, if applied at a global level, the root node of each decision tree may be the medical/procedure code (e.g., CPT code, HCPCS code, and/or the like). If applied at a line of business level and/or health plan product level, there may be a separate decision tree for each medical/procedure code (e.g., CPT code, HCPCS code, and/or the like) each line of business and/or health plan product. In these examples, it may first need to be determined what line of business and/or health plan product the request relates to for identifying of the appropriate decision tree.

In one embodiment, generated decision trees can be stored for later use. For example, decision trees can be stored as graph data structures and/or other data structures that can be accessed when needed to determine whether PAs are required. In such an embodiment, the graph data structures may have one or more entry points (e.g., nodes) and/or one or more relationships. For example, CPT code 42820 may be an entry node that connects to each line of business that uses the codes, each health plan that uses the code, and/or each client that uses the code. Thus, there may be multiple decisions trees that are identifiable from CPT code 42820 (e.g., node) using one or more relationships or attributes. Then, using the relationships or attributes from the corresponding PA request, the appropriate decision tree can be identified and traversed. For example, if the request identifies a line of business or a health plan product, the appropriate relationship to CPT code 42820 can be identified from the corresponding node and used to identify and traverse the appropriate tree. As will be recognized, there may be one or more nodes that can be used to identify an appropriate decision tree, such as CPT code and line of business, CPT code and member, CPT code and health plan product, and/or the like. In another embodiment, the decision trees can be generated in real-time in response to PA requests for making PA determinations.

In one embodiment, updated or new decisions trees can be generated in a manual, semi-automated, and/or automate manner. For example, when one or more fields of a row for a particular medical/procedure code (e.g., CPT code, HCPCS code, and/or the like) are changed, the corresponding decision tree can be updated or a new decision tree can be generated with the previous decision tree being discarded or stored for historical records. For instance, each time the authorization system 65 updates a field of a row/tuple, the authorization system 65 can automatically update the corresponding decision tree or generate a new decision tree. As will be recognized, a variety of approaches and techniques can be used to adapt to various needs and circumstances.

h. Receiving Requests and Providing Responses

In one embodiment, with the rows/tuples of the relational database populated and/or the decision trees generated and stored, the authorization system 65 can receive PA requests and provide PA responses (steps/operations 420, 422, 424, and 426 of FIG. 4B). Such requests are inquiries as to whether a PA is required for a particular procedure, service, product, device, and/or the like; for a particular member; with a particular provider; on a particular date; and/or at a particular location.

As noted previously, in one embodiment, the authorization system 65 may receive an initial PA request that identifies the medical/procedure code (e.g., CPT code, HCPCS code, and/or the like), business line, and/or health plan. In the initial PA response, the authorization system 65 may provide the attributes that need to be populated with discrete values in a subsequent request to allow for a PA determination. In this example, a subsequent PA request may include the relevant discrete values. The authorization system 65 can make an appropriate determination and provide subsequent PA response. The subsequent PA response indicates whether a PA is required for a particular procedure, service, product, device, and/or the like; for a particular member; with a particular provider; on a particular date; and/or at a particular location.

In another embodiment, the authorization system 65 may receive a PA request that identifies the medical/procedure code (e.g., CPT code, HCPCS code, and/or the like), business line, health plan, and/or the discrete values to allow for a PA determination. In this example, the authorization system 65 can identify the appropriate decision tree, make an appropriate determination, and provide an appropriate PA response. The PA response indicates whether a PA is required for a particular procedure, service, product, device, and/or the like; for a particular member; with a particular provider; on a particular date; and/or at a particular location.

Continuing with the above example, the following describes a traversal of decision tree 700 when the PA request is for CPT code 42820. A traversal of decision tree 700 begins at node 702, which is the node that identifies the CPT code 42820 to which the tree corresponds. The traversal automatically proceeds to node 704. At node 704, a determination is made (e.g., based on the discrete values provided in the request) as to whether the provider is a participating provider. If the provider is not a participating provider, the traversal automatically proceeds to node 706 that indicates a PA is required. If the provider is a participating provider, the traversal automatically proceeds to node 708. At node 708, determination is made (e.g., based on the discrete values provided in the request) as whether the place of service is an ambulatory surgery center. If the place of service is an ambulatory surgery center, the traversal automatically proceeds to node 712 that indicates a PA is not required. If the place of service is not an ambulatory surgery center, the traversal automatically proceeds to node 710 that indicates a PA is required.

i. Interactive Interfaces

As noted previously, the authorization system 65 may comprise or communicate with a variety of internal and/or external interfaces 214A-N. In one embodiment, the authorization system 65 may comprise or communicate with an installer/editor interface 214D.

The installer/editor interface 214D may be a web interface that manages and maintains PA requirements and their business products and associates business products to claims platform products. In one embodiment, installer/editor interface 214D provides a visual, user friendly interface that allows for visually configuring PA requirements instead of requiring technical coding of a decision tree or other data structure. The installer/editor interface 214D also provides for the auto population of or copying from known procedures and diagnosis codes and related descriptions and allows for health plan products to be pre-populated on creation with PA requirements for all procedure codes from existing health plan products.

In one embodiment, the authorization system 65 may also comprise or communicate with a reporter interface 214A and/or a viewer interface 214B. These interfaces may be web interfaces for generating and viewing preconfigured reports and configurable reports. These interfaces may also allow for data mining, comparison of business products, and/or the like. For example, the reporter interface may provide the ability search, filter, and sort PA requirements using the one or more RDBMSs, relational databases, relational database tables, lines of business, health plan products, and/or the like.

IV. CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
providing, by one or more processors, an interface enabling navigation of (a) one or more first prior authorization requirements and (b) one or more second prior authorization requirements, wherein (a) the one or more first prior authorization requirements correspond to a first medical code, and (b) the one or more second prior authorization requirements correspond to a second medical code;
populating, by the one or more processors, (a) one or more fields of a first row of a table of a relational database with at least a first portion of the one or more first prior authorization requirements and (b) one or more fields of a second row of the table of the relational database with at least a second portion of the one or more first prior authorization requirements, wherein at least one field in the first row comprises a null value;
populating, by the one or more processors, (a) one or more fields of a third row of the table of the relational database with at least a first portion of the one or more second prior authorization requirements and (b) one or more fields of a fourth row of the table of the relational database with at least a second portion of the one or more second prior authorization requirements;
generating, by the one or more processors, at least two decision tree data structures for storage in one or more graph databases based at least in part on the table of the relational database, wherein the at least two tree data structures comprise:
(i) a first decision tree data structure for the first medical code based at least in part on the first row and the second row, wherein the first decision tree data structure comprises a root node corresponding to the first medical code and one or more leaf nodes defining a shortest path from the first medical code to at least one prior authorization response for the first medical code, wherein the shortest path is based at least in part on a first field of the one or more fields of the first row and a second field of the one or more fields of the second row, wherein the null value causes a respective leaf node of the first decision tree data structure to not be generated for the at least one field; and
(ii) a second decision tree data structure for the second medical code based at least in part on the third row and the fourth row;
receiving, by the one or more processors, a prior authorization request for the first medical code;
responsive to receiving the prior authorization request, selecting, by the one or more processors, the first decision tree data structure from the at least two decision tree data structures;
traversing, by the one or more processors, the first decision tree data structure to identify a prior authorization response, wherein the prior authorization response is stored in a terminal node of the first decision tree data structure; and
providing, by the one or more processors, the prior authorization response.

2. The computer-implemented method of claim 1, wherein:
(a) the root node is a first root node, and
(b) a second root node of the second decision tree data structure comprises the second medical code.

3. The computer-implemented method of claim 1, wherein the prior authorization request is received via an application programming interface and the prior authorization response is provided via the application programming interface.

4. The computer-implemented method of claim 1, wherein the one or more fields of the first row are automatically populated.

5. The computer-implemented method of claim 1, wherein the first decision tree data structure is generated before receiving the prior authorization request.

6. A computer program product comprising a non-transitory computer readable medium having computer program instructions stored therein, the computer program instructions, when executed by one or more processors, cause the one or more processors to:
provide an interface enabling navigation of (a) one or more first prior authorization requirements and (b) one or more second prior authorization requirements, wherein (a) the one or more first prior authorization requirements correspond to a first medical code, and (b) the one or more second prior authorization requirements correspond to a second medical code;
populate (a) one or more fields of a first row of a table of a relational database with at least a first portion of the one or more first prior authorization requirements and (b) one or more fields of a second row of the table of the relational database with at least a second portion of the one or more first prior authorization requirements, wherein at least one field in the first row comprises a null value;

populate (a) one or more fields of a third row of the table of the relational database with at least a first portion of the one or more second prior authorization requirements and (b) one or more fields of a fourth row of the table of the relational database with at least a second portion of the one or more second prior authorization requirements;

generate at least two decision tree data structures for storage in one or more graph databases based at least in part on the table of the relational database, wherein the at least two tree data structures comprise:
  (i) a first decision tree data structure for the first medical code based at least in part on the first row and the second row, wherein the first decision tree data structure comprises a root node corresponding to the first medical code and one or more leaf nodes defining a shortest path from the first medical code to at least one prior authorization response for the first medical code, wherein the shortest path is based at least in part on a first field of the one or more fields of the first row and a second field of the one or more fields of the second row, wherein the null value causes a respective leaf node of the first decision tree data structure to not be generated for the at least one field; and
  (ii) a second decision tree data structure for the second medical code based at least in part on the third row and the fourth row;

receive a prior authorization request for the first medical code;

responsive to receiving the prior authorization request select the first decision tree data structure from the at least two decision tree data structures;

traverse the first decision tree data structure to identify a prior authorization response, wherein the prior authorization response is stored in a terminal node of the first decision tree data structure; and provide the prior authorization response.

7. The computer program product of claim 6, wherein:
(a) the root node is a first root node, and
(b) a second root node of the second decision tree data structure comprises the second medical code.

8. The computer program product of claim 6, wherein the prior authorization request is received via an application programming interface and the prior authorization response is provided via the application programming interface.

9. The computer program product of claim 6, wherein the one or more fields of the first row are automatically populated.

10. The computer program product of claim 6, wherein the first decision tree data structure is generated before receiving the prior authorization request.

11. A computing system comprising a non-transitory computer readable storage medium and one or more processors, the computing system configured to:
provide an interface enabling navigation of (a) one or more first prior authorization requirements and (b) one or more second prior authorization requirements, wherein (a) the one or more first prior authorization requirements correspond to a first medical code, and (b) the one or more second prior authorization requirements correspond to a second medical code;

populate (a) one or more fields of a first row of a table of a relational database with at least a first portion of the one or more first prior authorization requirements and (b) one or more fields of a second row of the table of the relational database with at least a second portion of the one or more first prior authorization requirements, wherein at least one field in the first row comprises a null value;

populate (a) one or more fields of a third row of the table of the relational database with at least a first portion of the one or more second prior authorization requirements and (b) one or more fields of a fourth row of the table of the relational database with at least a second portion of the one or more second prior authorization requirements;

generate at least two decision tree data structures for storage in one or more graph databases based at least in part on the table of the relational database, wherein the at least two tree data structures comprise:
  (i) a first decision tree data structure for the first medical code based at least in part on the first row and the second row, wherein the first decision tree data structure comprises a root node corresponding to the first medical code and one or more leaf nodes defining a shortest path from the first medical code to at least one prior authorization response for the first medical code, wherein the shortest path is based at least in part on a first field of the one or more fields of the first row and a second field of the one or more fields of the second row, wherein the null value causes a respective leaf node of the first decision tree data structure to not be generated for the at least one field; and
  (ii) a second decision tree data structure for the second medical code based at least in part on the third row and the fourth row for storage in the one or more graph databases;

receive a prior authorization request for the first medical code;

responsive to receiving the prior authorization request select the first decision tree data structure from the at least two decision tree data structures;

traverse the first decision tree data structure to identify a prior authorization response, wherein the prior authorization response is stored in a terminal node of the first decision tree data structure; and provide the prior authorization response.

12. The computing system of claim 11, wherein:
(a) the root node is a first root node, and
(b) a second root node of the second decision tree data structure comprises the second medical code.

13. The computing system of claim 11, wherein the prior authorization request is received via an application programming interface and the prior authorization response is provided via the application programming interface.

* * * * *